United States Patent
Dumas et al.

(10) Patent No.: US 12,011,501 B2
(45) Date of Patent: Jun. 18, 2024

(54) COMPOSITION COMPRISING A LACTOBACILLUS RHAMNOSUS EXTRACT

(71) Applicant: L V M H Recherche, Saint Jean de Braye (FR)

(72) Inventors: Marc Dumas, Saint Jean le Blanc (FR); Catherine Heusele, Limours (FR); Valérie Gorzelanczyk, Saint Jean le Blanc (FR); Olivier Jeanneton, Vitry Aux Loges (FR)

(73) Assignee: L V M H Recherche, Saint Jean de Braye (FR)

( * ) Notice: Subject to any disclaimer, the term of this patent is extended or adjusted under 35 U.S.C. 154(b) by 220 days.

(21) Appl. No.: 17/415,585

(22) PCT Filed: Dec. 18, 2019

(86) PCT No.: PCT/EP2019/086091
§ 371 (c)(1),
(2) Date: Jun. 17, 2021

(87) PCT Pub. No.: WO2020/127581
PCT Pub. Date: Jun. 25, 2020

(65) Prior Publication Data
US 2022/0054401 A1    Feb. 24, 2022

(30) Foreign Application Priority Data

Dec. 21, 2018 (FR) ........................ 1873831

(51) Int. Cl.
*A61K 35/747* (2015.01)
*A61K 8/99* (2017.01)
*A61Q 17/00* (2006.01)
*A61Q 19/08* (2006.01)

(52) U.S. Cl.
CPC ................ *A61K 8/99* (2013.01); *A61Q 17/00* (2013.01); *A61Q 19/08* (2013.01)

(58) Field of Classification Search
CPC .................................................... A61Q 19/08
See application file for complete search history.

(56) References Cited

U.S. PATENT DOCUMENTS

| 2012/0301452 A1 | 11/2012 | Gueniche et al. |
| 2015/0079040 A1* | 3/2015 | O'Neill ................ A61K 35/745 424/93.3 |
| 2016/0051601 A1 | 2/2016 | Rios et al. |

FOREIGN PATENT DOCUMENTS

| CN | 107126519 A * | 9/2017 |
| CN | 108125905 A | 6/2018 |
| EP | 2332520 A1 | 6/2011 |
| FR | 3004349 A1 | 10/2014 |
| KR | 20140013797 A | 2/2014 |
| KR | 20140076538 A * | 6/2014 |
| WO | WO-2011029784 A1 | 3/2011 |
| WO | WO-2013153358 A1 | 10/2013 |
| WO | WO-2013154407 A1 | 10/2013 |
| WO | WO-2015012421 A1 | 1/2015 |

OTHER PUBLICATIONS

International Search Report dated Mar. 26, 2020 in International Application No. PCT/EP2019/086091.
English translation of Chinese Office Action issued in corresponding Chinese Patent Application No. 2023032102050670 (dated Mar. 21, 2023).
Nissila et al., Genotypic and phenotypic diversity of Lactobacillus rhamnosus clinical isolates, their comparison with strain GG and their recognition by complement system, 12(5) PLoS ONE 1-18 (May 11, 2017).

* cited by examiner

*Primary Examiner* — Qiuwen Mi
(74) *Attorney, Agent, or Firm* — Panitch Schwarze Belisario & Nadel LLP; Erin M. Dunston

(57) ABSTRACT

The present invention concerns a composition for topical application to keratinous material, in particular the skin and/or lips, comprising, in a physiologically acceptable medium, at least one *Lactobacillus rhamnosus* extract (CNCM I-5313), one of its fractions and/or one of its metabolites and at least one excipient chosen from solvents other than water, UV filters, surfactants, gelling agents, thickeners, fillers, dyes, film-forming polymers, perfumes and the mixtures of same; and the uses thereof, in particular for promoting and/or improving the skin barrier function.

6 Claims, No Drawings

COMPOSITION COMPRISING A LACTOBACILLUS RHAMNOSUS EXTRACT

CROSS-REFERENCE TO RELATED APPLICATIONS

This application is a U.S. National Stage Application pursuant to 35 U.S.C. § 371 of International Patent Application PCT/EP2019/086091, filed on Dec. 18, 2019, and published as WO 2020/127581 on Jun. 25, 2020, which claims priority to French Patent Application No. 1873831, filed on Dec. 21, 2018, all of which are incorporated herein by reference in their entireties for all purposes.

FIELD OF THE INVENTION

The present invention concerns a composition comprising a novel extract of *Lactobacillus rhamnosus*, in particular a *Lactobacillus rhamnosus* lysate (CNCM I-5313), and its beneficial effects on keratinous material, in particular the skin.

STATE OF THE ART

The skin is the primary barrier for the human body. It protects the organs from temperature and humidity differences and damage from the external environment, such as UV radiation, stress, pollution, pathogenic microorganisms, etc. However, excessive chemical and physical stimulation deteriorate the normal functions of the skin and induce or accelerate its aging, leading to the appearance of wrinkles and a loss of firmness, suppleness and elasticity.

The search for new molecules or active ingredients usable in cosmetics is a necessity to develop effective products to give the skin a younger appearance and a more even complexion, with no irregular coloration from pigmentation or microcirculation, a radiant complexion.

The Applicant has rightly demonstrated that a *Lactobacillus rhamnosus* extract, in particular a *Lactobacillus rhamnosus* lysate (CNCM I-5313), had beneficial effects on skin cultures in vitro.

The Applicant demonstrated that this lysate had a stimulating effect on the expression of several genes especially involved in:
  detoxification (MRP1=ABCC1, LONP1, GPX1),
  the functioning of the mitochondrial respiratory chain involved in the production of cellular energy (MT=NADH dehydrogenase/ubiquinone),
  the secretion of hyaluronic acid (MRP5),
  the maintenance of the integrity of cell structures, such as the cell nucleus (SYNE2, LMNA), and
  the formation of several collagens and elastin (COL1A1, COL5A1, COL13A1, ELN).

Thus, the *Lactobacillus rhamnosus* extract according to the invention and, in particular a *Lactobacillus rhamnosus* lysate (CNCM I-5313), is advantageous in that it exhibits a detoxifying and antioxidant effect, an antiaging effect targeting the reduction of wrinkles and loss of firmness and density (collagens and elastin and anchoring points between cells and these protein structures), a skin-strengthening effect (cell structures such as the cell nucleus) an effect of adapting the skin to hypoxic stress, a depigmentation effect on skin spots (melanogenesis inhibition) and/or an effect of normalizing the skin microbiota via the reinforcement of innate immunity and the skin barrier.

DISCLOSURE OF THE INVENTION

A first subject of the invention concerns a composition for topical application on keratinous materials, in particular the skin and/or lips, comprising, in a physiologically-acceptable medium, at least one *Lactobacillus rhamnosus* extract (CNCM I-5313), one of its fractions and/or one of its metabolites and at least one excipient chosen from among solvents other than water, UV filters, surfactants, gelling agents, thickeners, fillers, dyes, film-forming polymers, fragrances and mixtures thereof, in particular solvents other than water, surfactants, gelling agents, thickeners, fillers, dyes, film-forming polymers, fragrances and mixtures thereof.

The invention also relates to a non-therapeutic cosmetic method comprising the application on keratinous materials of at least one *Lactobacillus rhamnosus* extract (CNCM I-5313) according to the invention or a composition containing it, intended to prevent and/or reduce the signs of skin aging and/or promote and/or improve the barrier function. The terms *Lactobacillus rhamnosus* (CNCM I-5313) or *Lactobacillus rhamnosus* CNCM I-5313 are used interchangeably, corresponding to the *Lactobacillus rhamnosus* strain filed according to the Budapest Treaty with the National Collection of Cultures of Microorganisms (CNCM) at the Institut Pasteur (28 rue du Docteur Roux, F-75024 Paris cedex 15) on 11 Apr. 2018 in the name of BIOVITIS, Le Bourg, 15400 SAINT-ETIENNE-DE-CHOMEIL, under the designation under number [sic] CNCM I-5313.

The invention also relates to a non-therapeutic cosmetic use of a *Lactobacillus rhamnosus* extract (CNCM I-5313) to promote and/or improve the barrier function and/or reduce the signs of skin aging.

DETAILED DESCRIPTION OF THE INVENTION

The present invention therefore especially relates to a composition for topical application on keratinous materials, in particular the skin and/or the lips, comprising, in a physiologically-acceptable medium, at least one *Lactobacillus rhamnosus* extract (CNCM I-5313), one of its fractions and/or one of its metabolites and at least one excipient chosen from among solvents other than water, surfactants, gelling agents, thickeners, fillers, dyes, film-forming polymers, fragrances and mixtures thereof.

According to the invention, "keratinous materials" means the skin, mucosa (in particular the lips) and integuments. According to a particular embodiment, the composition is intended for topical application on the skin, lips or integuments, preferably the skin.

"Keratinous materials" according to the invention are generally healthy keratinous materials, i.e., not presenting conditions or disorders that would result from a pathological state ("unhealthy" subjects suffering from a pathology). The expressions healthy skin and/or lips or skin and/or lips are used interchangeably in the remainder of the description.

"Physiologically-acceptable medium" means a medium compatible with keratinous materials, in particular skin and/or lips.

According to the invention, "excipient" means a substance lacking cosmetic effect as such, but useful for the incorporation of the *Lactobacillus rhamnosus* extract into the composition of the invention or the formulation thereof.

*Lactobacillus rhamnosus* Extract

According to the definitions used by international scientific associations for probiotics and prebiotics, "probiotic" means living microorganisms that, when they are administered in an appropriate quantity, have beneficial effects on the health of the host. "Prebiotics" means food ingredients resisting digestion that induce specific changes in the composition and/or activity of the intestinal microbiota, thus producing a beneficial effect on the host. "Symbiotics" means products containing both probiotics and prebiotics.

The *Lactobacillus rhamnosus* extract (probiotic microorganism) according to the invention can be included in a composition according to the invention in a living, semi-active or inactivated, dead form. It can be included in the form of fractions of cellular components or in the form of metabolites. The microorganism, metabolite(s) or fractions) can also be introduced in the form of a lyophilized powder, a culture supernatant and/or, as applicable, in a concentrated form.

According to a particular embodiment, the *Lactobacillus rhamnosus* microorganism is implemented in the inactivated, or dead, form, more particularly in the form of a lysate.

Thus, according to a particular and preferred embodiment, the *Lactobacillus rhamnosus extract according to the invention is a Lactobacillus rhamnosus* lysate (CNCM I-5313) (non-living), one of its fractions and/or one of its metabolites.

The terms "probiotic extract" or "*Lactobacillus rhamnosus* extract" or "probiotic lysate" or "*Lactobacillus rhamnosus* lysate" will be used interchangeably.

Lysate especially means a material obtained by cellular lysis of the cells of the microorganism considered, thus inducing the release of the intracellular biological constituents naturally contained in said cells. The lysate implemented is formed of all or part of the intracellular biological constituents and the constituents of the cell walls and membranes. The present invention therefore concerns a probiotic lysate and/or one of its fractions and/or one of its metabolites.

Within the meaning of the invention, the term "fraction" more particularly designates a fragment of said microorganism endowed with the same beneficial effects on the skin, at least partially, by analogy with said whole microorganism.

In particular, the lysate according to the invention contains the cell cytoplasm fraction containing enzymes (e.g., dehydrogenases, phosphatases, etc.) and/or cell wall constituents (e.g., peptidoglycans, etc.) and/or cell membrane constituents (e.g., glycerophospholipids, etc.).

The cells can be lysed by different techniques well known to the skilled person, such as, for example, osmotic shock, thermal shock, by ultrasound, or even under mechanical stress (e.g., centrifugation).

According to a preferred embodiment, the lysate is obtained by centrifugation and osmotic shock (e.g., addition of sodium hydroxide).

According to a particular embodiment, the microorganism is cultivated anaerobically in an appropriate culture medium. When the stationary phase of growth is reached, the culture medium can be inactivated by pasteurization, for example at a temperature of 60 to 65° C. for 30 min. The microorganisms are then harvested by a conventional separation technique, for example membrane filtration, centrifugation and resuspension in a physiologically sterile NaCl solution. The lysate can be obtained by ultrasonic disintegration of such a medium in order to release the cytoplasm fractions, the fragments of the cell wall and the products derived from metabolism. Then all the components in their natural distribution are stabilized in a weakly acidic solution.

The lysate thus obtained generally has a concentration of around 0.1 to 10%, in particular from 0.5 to 5% and especially from 1 to 2% by weight of active dry matter relative to its total weight.

The lysate can then be implemented in different forms, in the form of a solution or in the form of a powder.

According to a particular embodiment, the lysate is in the form of a solution, preferably an aqueous solution, comprising from 0.1 to 10%, in particular from 0.5 to 5% and especially from 1 to 2% by weight of active dry matter relative to its total weight.

The probiotic microorganism according to the invention belongs to the species *Lactobacillus rhamnosus* (ATCC 7469, CCM 1825, NCDO 243, NCIB 6375 or WDCM 00101, depending on the collections in which it was filed), preferably the *Lactobacillus rhamnosus* CNCM I-5313 strain filed according to the Budapest Treaty with the National Collection of Cultures of Microorganisms (CNCM) at the Institut Pasteur (28 rue du Docteur Roux, F-75024 Paris cedex 15) on 11 Apr. 2018 in the name of BIOVITIS, Le Bourg, 15400 SAINT-ETIENNE-DE-CHOMEIL, under the designation CNCM I-5313, and/or one of its fractions and/or one of its metabolites.

A lysate of this *L. rhamnosus* strain is obtained according to the following protocol from the supplier, Greentech:
1. Culture of the *L. rhamnosus* strain in an appropriate culture medium;
2. Recovery of the biomass by centrifugation;
3. Cell lysis (addition of sodium hydroxide);
4. Adjustment of pH (addition of citric acid) and dry matter (addition of sterile water) to obtain an active material content ranging from 0.1 to 10% by weight of dry matter (active material) relative to the total weight of said lysate;
5. Addition of preservative (phenoxyethanol).

Such an *L. rhamnosus* lysate is called Probiophyte LB by the supplier, Greentech, and defined by its INCI name, WATER and *LACTOBACILLUS* FERMENT LYSATE and PHENOXYETHANOL and SODIUM HYDROXIDE and CITRIC ACID; phenoxyethanol can be replaced by another preservative.

This lysate comprises a *Lactobacillus rhamnosus* content ranging from 0.1 to 10%, in particular from 0.5 to 5% by weight and especially from 1 to 2% by weight of dry matter (active material) relative to the total weight of said lysate.

The *L. rhamnosus* lysate of the invention can be formulated in a composition in an amount of at least 0.0001% (expressed by dry weight or weight of active material), in particular an amount of from 0.0001 to 10% and more particularly an amount of from 0.0001 to 5% by weight, particularly 0.0001 to 2% by weight and especially 0.0001% to 1%, or even 0.0001 to 0.05% by weight relative to the total weight of the composition.

According to one particular embodiment, the *Lactobacillus rhamnosus* extract (CNCM I-5313) is present in a content ranging from 0.0001 to 0.05% by weight of active material relative to the total weight of said composition.

The *L. rhamnosus* lysate according to the invention can be used alone or associated with other probiotic microorganisms, prebiotic ingredients, symbiotic ingredients or mixtures thereof.

According to a particular embodiment, the composition also comprises at least one cosmetic active agent other than vitamins or extracts containing them, in particular chosen from oils rich in essential fatty acids or otherwise, prebiotic extracts (which facilitate the growth of certain beneficial bacterial species of the skin microflora to the detriment of undesirable species), other extracts of other strains of probiotic microorganisms or even symbiotic ingredients (probiotic extracts+prebiotic extracts), sebum regulators (to promote the biodiversity of the flora) and firming agents (to limit pore enlargement), soothing agents, protective active ingredients, in particular stimulators of antioxidant and detoxifying defenses of the skin (otherwise known as antioxidant agents or simply antioxidants), depigmenting agents, exfoliating agents, anti-aging active ingredients, moisturizing ingredients, immunomodulatory active ingredients, and mixtures thereof.

"Composition" according to the invention means a cosmetic or dermatological composition. According to one particular embodiment, it will be a cosmetic composition.

According to another particular embodiment, it will be a dermatological composition.

The composition according to the invention can, for example, be used as a care and/or makeup product for the face and/or body.

The compositions according to the invention are intended more particularly for topical application on keratinous materials, in particular on the skin.

The compositions of the invention comprise a physiologically-acceptable medium, i.e., compatible with skin and integuments. The compositions can have all cosmetic forms, and especially be in the form of an oil-in-water or water-in-oil emulsion or multiple emulsion, a microemulsion, a solution, a suspension, a lotion, a gel, a cream, a milk, a serum, a mist (sprayed fluid solution), a stick or even a powder and suitable for application to the skin, lips and/or integuments.

According to a particular embodiment, the composition of the invention is intended for topical application on the skin and/or lips and is present in the form of a cosmetic care composition and/or a makeup composition for the skin, and/or lips.

The cosmetic composition of the invention is advantageously in the form of an emulsion, serum or mist.

The composition generally comprises at least one aqueous phase and at least one oily phase. The aqueous phase generally represents from 1 to 99% by weight with regard to the total weight of said composition.

An oily phase according to the invention can comprise hydrocarbon oils, silicone oils, fluorinated or nonfluorinated, and mixtures thereof. These oils can be volatile or nonvolatile, vegetable, mineral or synthetic.

Advantageously, hydrocarbon oils will be used, especially of plant origin.

Volatile hydrocarbon oils include C8-C16 branched alkanes, C8-C16 branched esters and mixtures thereof.

Nonvolatile hydrocarbon oils include, in particular, hydrocarbon oils, vegetable hydrocarbon oils, C10-C40 synthetic ethers, C10-C40 synthetic esters, C12-C26 fatty alcohols, C12-C22 higher fatty acids, and mixtures thereof.

The oils can be present in the composition of the invention in a content ranging from 1 to 95% by weight relative to the total weight of the composition.

The composition of the invention can also comprise any additive usually used in cosmetics, such as UV filters, antioxidants, surfactants, gelling agents, fillers, dyes (e.g., pigments), preservatives, film-forming polymers, fragrances, cosmetic active ingredients, such as, for example, emollients, moisturizers, vitamins, anti-aging agents, lightening agents and mixtures thereof.

Cosmetic Method and Other Uses

The invention also relates to a non-therapeutic cosmetic method intended to prevent and/or reduce the signs of skin aging and/or promote and/or improve the barrier function, comprising the application on keratinous materials of at least one *Lactobacillus rhamnosus* extract (CNCM 1-5313) in particular a *Lactobacillus rhamnosus* lysate (CNCM I-5313), one of its fractions and/or one of its metabolites, or a composition according to the invention such as defined previously.

Preferably, the keratinous materials according to the invention are healthy keratinous materials.

The *Lactobacillus rhamnosus* extract is generally present in a content ranging from 0.0001 to 10% by weight of dry matter, in particular 0.0001 to 5%, preferably 0.0001 to 2%, and especially 0.0001% to 1%, or even 0.0001 to 0.05% by weight relative to the total weight of the composition.

The composition implemented in the cosmetic method can be a care and/or makeup composition, in particular a skincare composition for the face and/or body.

In particular, the method is intended to prevent and/or reduce loss of skin firmness and density, prevent and/or reduce the appearance of wrinkles and/or fine lines and/or skin spots, improve skin radiance and/or evenness, promote and/or improve skin hydration, detoxify the skin, promote and/or stimulate its antioxidant defenses and/or improve resistance of the skin to hypoxia, and/or control skin microflora, and/or stimulate skin immunity and the formation of the skin barrier.

"Promote and/or stimulate antioxidant defenses of keratinous materials" especially means to promote skin oxygenation and thus reduce the effects of skin hypoxia and to promote cellular respiration and energy production at the cellular level.

"Promote and/or stimulate skin immunity" means to maintain the balance of skin microflora and promote skin homeostasis for healthier skin that is better protected from external agents.

According to a particular embodiment, the method is intended to prevent and/or reduce loss of skin firmness and density, prevent and/or reduce the appearance of wrinkles and/or fine lines and/or skin spots, improve skin radiance and/or evenness, promote and/or improve skin hydration and/or improve resistance of the skin to hypoxia, and/or control skin microflora.

According to a particular embodiment, the composition of the invention is applied onto aged, lackluster, tired skin or skin impacted by an unfavorable or unbalanced diet, emotional stress or lack of sleep.

The present invention also relates to the non-therapeutic cosmetic use of a *Lactobacillus rhamnosus* extract (CNCM I-5313) to promote and/or improve its barrier function and/or reduce signs of skin aging, in particular to prevent and/or reduce loss of skin firmness and density, prevent and/or reduce the appearance of wrinkles and/or fine lines and/or skin spots, improve skin radiance and/or evenness, promote and/or improve skin hydration, detoxify the skin, stimulate its antioxidant defenses and/or improve resistance of the skin to hypoxia, and/or control skin microflora, and/or stimulate skin immunity and the formation of the skin barrier.

According to a particular embodiment, the extract according to the invention is used to promote and/or improve the barrier function and/or reduce signs of skin aging, in particular to prevent and/or reduce loss of skin firmness and density, prevent and/or reduce the appearance of wrinkles and/or fine lines and/or skin spots, improve skin radiance and/or evenness, promote and/or improve skin hydration, detoxify the skin and/or improve resistance of the skin to hypoxia, and/or control skin microflora.

The invention also relates to a *Lactobacillus rhamnosus* extract CNCM I-5313 according to the invention to promote and/or stimulate skin immunity.

The invention now will be illustrated in the following nonlimiting examples.

Unless otherwise indicated, the percentages are expressed as percentage by weight relative to the total weight of the composition.

Examples

The Applicant has assessed the effect of a lysate of the probiotic bacterial strain *L. rhamnosus*: ATCC 7469, CCM 1825, NCDO 243, NCIB 6375 or WDCM 00101, depending on the collections in which it was filed.

In particular, the probiotic bacterial strain used was filed according to the Budapest Treaty with the National Collection of Cultures of Microorganisms (CNCM) at the Institut Pasteur (28 rue du Docteur Roux, F-75024 Paris cedex 15) on 11 Apr. 2018 in the name of BIOVITIS, Le Bourg, 15400 SAINT-ETIENNE-DE-CHOMEIL, under the designation CNCM I-5313.

A lysate of this *L. rhamnosus* strain is obtained according to the following protocol from the supplier, Greentech:
1. Culture of the *L. rhamnosus* strain in an appropriate culture medium;
2. Recovery of the biomass by centrifugation;
3. Cell lysis (addition of sodium hydroxide);
4. Adjustment of pH (addition of citric acid) and dry matter (addition of sterile water) to obtain an active material content ranging from 0.01 to 10% by weight of dry matter (active material) relative to the total weight of said lysate;
5. Optional addition of preservative (e.g., phenoxyethanol).

Such an *L. rhamnosus* lysate is named Probiophyte LB by the supplier, Greentech, and defined by INCI name as WATER and *LACTOBACILLUS* FERMENT LYSATE and PHENOXYETHANOL and SODIUM HYDROXIDE and CITRIC ACID; the phenoxyethanol can be replaced by another preservative.

This lysate comprises a *Lactobacillus rhamnosus* content ranging from 0.1 to 10%, in particular from 0.5 to 5% by weight and especially from 1 to 2%, even 1.75% by weight of dry matter (active material) relative to the total weight of said lysate.

Such a lysate (but without the phenoxyethanol preservative) is tested at a content of 0.05, 0.1 and 0.2% in tests on skin cell cultures and used in the cosmetic compositions for topical application illustrated below in contents ranging from 1 to 2% by weight of raw material.

The terms Probiophyte LB or *Lactobacillus rhamnosus* lysate are used interchangeably in the following examples.

Example 1: Effect of the *L. rhamnosus* Extract on Keratinocyte Cultures

The test implemented here made it possible to compare two probiotic bacterial strain extracts in order to select the most effective extract to stimulate skin cells. RT-qPCR methodology was used, which makes it possible to observe the stimulation or inhibition or even absence of stimulation of genes involved in key skincare processes, in particular keratinocytes, the predominant cells of the epidermis.

Normal human keratinocytes (NHK) are cultured and then treated with the *L. rhamnosus* probiotic extract described above or *Lactococcus lactis* extract.

After treating the NHK, a polymerase chain reaction (qPCR) study is done on the genes studied from cDNA obtained after reverse transcription of the total RNA extracted.

Cells Used and Culture Conditions:
Cells: third passage normal human keratinocytes (NHEK)
Culture medium: Keratinocyte-SFM supplemented with 0.25 ng/ml EGF, 25 µg/ml pituitary extract and 25 µg/ml gentamycin at 37° C. and with 5% CO2
Test medium: Keratinocyte-SFM supplemented with 25 µg/ml gentamycin
Compounds Tested:
Probiophyte LB without preservative: *Lactobacillus rhamnosus* extract CNCM I-5313 according to the invention
*Lactococcus lactis* extract: *Lactococcus lactis* extract provided by Greentech (product ref. 001119, batch no. LYCC1204E1-BY of March 2012) and comprising a *Lactococcus lactis* lysate, citric acid and sodium hydroxide. The dry matter (active) content of *L. lactis* is from 5 to 6% by weight of raw material.
Doses tested: 0.05, 0.1 and 0.2%
Treatment time: 24 h
N=3 cultures per experimental condition Analyses Performed:
Measurement of gene expression by RT-qPCR on messenger RNA extracts from untreated cell layers (controls) and those treated with various concentrations of the probiotic extract. Several genes were assessed. The genes and the corresponding results are presented in the tables below, for which differential results were observed between the extract according to the invention (Probiophyte LB: *Lactobacillus rhamnosus*) extract and the comparative extract (*Lactococcus lactis* extract).

RT-qPCR (RT-Quantitative PCR) Technology

Obtaining Total RNA

The total RNA of each sample were isolated using TriPure Isolation Reagent® according to the protocol recommended by the supplier. The quantity and quality of RNA were evaluated by capillary electrophoresis (Bioanalyzer 2100, Agilent).

Potential traces of contaminant DNA were eliminated by treatment with the DNA-free system (Ambion).

Synthesis of Complementary DNA

Complementary DNA (cDNA) was synthesized by reverse transcription of total RNA in the presence of oligo (dT) and the "Transcriptor First strand cDNA Synthesis" enzyme (Roche Diagnostics). The cDNA obtained was quantified by spectrophotometry (Nanovue; GE Healthcare), then the quantity of cDNA was adjusted to 5 ng/µl.

Quantitative PCR

The polymerase chain reactions (PCR) were done by quantitative PCR (Light Cycler; Roche Molecular Systems Inc.) and according to the procedures recommended by the supplier.

The reaction mixture (10 µl final) for each sample contained:
  2.5 µl of cDNA at 5 ng/µl,
  the primers for the various markers used,
  the reaction medium containing taq DNA polymerase enzyme, SYBR Green I marker and MgCl2.

Data Processing and Statistical Analysis

The crude data were transferred and processed by Microsoft Excel®.

The incorporation of fluorescence into the amplified DNA is measured continuously during the PCR cycles. These measurements make it possible to obtain fluorescence intensity curves as a function of PCR cycles and thus assess a relative expression (RE) value for each marker.

The number of cycles is determined from "output" points of the fluorescence curves. For the same marker analysed, the later the sample (higher number of cycles), the lower the initial number of mRNA copies.

The relative expression (RE) value is expressed in arbitrary units (AU) according to the following formula:

$$(\frac{1}{2}^{number\ of\ cycles}) \times 10^6$$

strengthening of the dermal-epidermal junction with stimulation of the type 7 collagen gene (COL7A1), a collagen for adhesion between the dermis and the epidermal junction. This collagen is reduced during aging.

TABLE 1

Genes studied

| | Genes | | |
|---|---|---|---|
| | Gene name and origin | NCBI reference | Abbreviation |
| Housekeeping genes (references) | Ribosomal protein S28 (human) | Gene ID: 6234 | RPS28 |
| | Glyceraldehyde-3-phosphate-dehydrogenase (human) | Gene-ID: 2597 | GAPDH |
| Keratinocyte differentiation | Transglutaminase 1 (K polypeptide epidermal type I, protein-glutamine-gamma-glutamyltransferase) (human) | Gene ID: 7051 | TGM1 |
| Antimicrobial peptide, innate immunity | S100 calcium binding protein A7 (human) | Gene ID: 6278 | S100A7 |
| | Peptidase inhibitor 3, skin-derives(human) | Gene ID: 5266 | PI3 |
| | Ribonuclease, RNAse A family, 7 (human) | Gene ID: 84659 | RNASE7 |
| Extracellular matrix | Collagen, type VII, alpha 1 | Gene ID: 1294 | COL7A1 |

TABLE 2

| Genes | Control Cycles | Probiophyte LB (*L. rhamnosus*) 0.05% | | Probiophyte LB (*L. rhamnosus*) 0.1% | | Probiophyte LB (*L. rhamnosus*) 0.2% | | *L. lactis* 0.05% | | *L. lactis* 0.1% | | *L. lactis* 0.2% | |
|---|---|---|---|---|---|---|---|---|---|---|---|---|---|
| | | Cycles | % Control (HK mean) 100 | Cycles | % Control (HK mean) 100 | Cycles | % Control (HK mean) 100 | Cycles | % Control (HK mean) 100 | Cycles | % Control (HK mean) 100 | Cycles | % Control (HK mean) 100 |
| RP S28 | 18.97 | 18.82 | 98 | 18.82 | 117 | 19.02 | 99 | 19.13 | 97 | 19.25 | 89 | 19.18 | 88 |
| | 18.95 | 19.07 | | 18.99 | | 19.07 | | 19.15 | | 19.10 | | 19.44 | |
| GAPDH | 17.31 | 17.30 | 101 | 17.67 | 94 | 17.53 | 100 | 17.46 | 101 | 17.49 | 104 | 17.51 | 104 |
| | 17.43 | 17.31 | | 17.59 | | 17.35 | | 17.51 | | 17.24 | | 17.45 | |
| TGM1 | 31.62 | 29.90 | 265 | 30.19 | 291 | 29.60 | 416 | 31.07 | 151 | 31.21 | 122 | 30.63 | 204 |
| | 31.51 | 30.35 | | 30.21 | | 29.56 | | 31.14 | | 31.45 | | 30.78 | |
| S100A7 | 30.79 | 30.14 | 150 | 30.46 | 131 | 29.21 | 308 | 30.70 | 120 | 30.71 | 99 | 30.64 | 129 |
| | 30.81 | 30.19 | | 30.72 | | 29.29 | | 30.64 | | 31.01 | | 30.56 | |
| PI3 | 26.16 | 26.15 | 102 | 25.67 | 151 | 25.00 | 214 | 26.12 | 104 | 26.61 | 70 | 26.04 | 113 |
| | 26.12 | 25.96 | | 25.78 | | 25.24 | | 26.31 | | 26.79 | | 26.23 | |
| RNASE7 | 27.06 | 26.28 | 164 | 26.49 | 183 | 26.29 | 209 | 27.64 | 86 | 28.49 | 42 | 28.80 | 40 |
| | 27.42 | 26.67 | | 26.57 | | 26.19 | | 27.51 | | 28.57 | | 28.64 | |
| COL7A1 | 28.50 | 27.33 | 220 | 27.64 | 231 | 27.55 | 214 | 27.71 | 198 | 29.33 | 71 | 29.22 | 84 |
| | 28.73 | 27.51 | | 27.52 | | 27.62 | | 27.80 | | 28.99 | | 28.87 | |

Results show the stimulant effect of Probiophyte LB according to the invention on several keratinocyte genes compared to the *Lactococcus lactis* extract.

The table above shows the stimulant effect of Probiophyte LB on several important skin processes:

the formation of the skin barrier with stimulation of the transglutaminase (TGM1) gene that enables the formation of the cornified envelopes of corneocytes which ensure the mechanical and chemical resistance and hydrophobicity of the skin surface as well as the organization of lipids on the skin surface;

innate immunity with stimulation of several genes for antimicrobial peptides that make it possible to control the development of skin microflora: DEFB4A, S100A7, PI3, RNASE7, and Example 2: Effect of the *L. rhamnosus* Extract on Keratinocyte, Melanocyte and Fibroblast Cultures This second experiment allows in-depth study of the biological effects of Probiophyte LB, TaqMan low density array (TLDA) methodology on a larger repertoire of genes and on the three main cell types of the skin: keratinocytes, melanocytes, and fibroblasts.

Cells Used:

Fifth passage normal human keratinocytes (NHK), sixth passage normal human fibroblasts and seventh passage normal human melanocytes (NHM)

Compounds Tested:

Probiophyte LB without preservative: *Lactobacillus rhamnosus* CNCM I-5313 extract Doses tested: 0.1 and 0.2 μg/ml
Treatment time: 24 h
N=3 cultures per experimental condition
Analyses Performed:
Measurement of gene expression by RT-qPCR from messenger RNA extracts from untreated cell layers (controls) and those treated with various concentrations of Probiophyte LB.

TaqMan Low Density Array (TLDA) Technology

Obtaining Total RNA

The cell culture medium is eliminated and 250 μL of RLT lysis buffer (provided in the Nucleospin RNA trace kit, Macherey-Nagel) are added. The cells are scraped with a cell scraper and then the cell lysate is recovered in a 1.2 mL deep well (provided in the NucleoSpin RNA kit). The total RNA is extracted according to the protocols defined.

The total RNA solutions obtained are assayed and their quality verified using a microplate reader, SPECTROstar Nano (BMG Labtech) paired with the Microlab STAR. This device is connected to the computer controlling the robotic platform and has specific software for analysis of results (MARS). The technique requires a 384-well microplate (LoBase) and a positive control (RNA 250, AM7155, ThermoFisher) to validate the pipetting done by the robot and the values generated by the SPECTROstar Nano reader.

Synthesis of Complementary DNA

The reverse transcription (RT) kit used is the High Capacity Reverse Transcription Kit (ThermoFisher). It was used according to the protocol provided. 500 ng of total RNA are diluted in water for a final volume of 25 μL. It is then incubated for 10 minutes at 25° C. then 2 hours at 37° C. in the presence of 25 μL of High Capacity Reverse Transcription Kit 2× reaction mixture previously prepared as indicated below. The different incubations are done in the TRobot (Biométra).

TABLE 3

| Reagents | RT buffer | dNTP | Primer | RNase OUT | RT | H2O |
|---|---|---|---|---|---|---|
| Volume | 5 μl | 2 μl | 5 μl | 0.5 μl | 2.5 μl | 10 μl |

High Capacity Reverse Transcription Kit 2× reaction medium for 1 reaction

PCR-TaqMan Low Density Array

15 μL of each RT are mixed with 60 μl of water then 75 μL of TaqMan Gene Expression master mix (ThermoFisher), containing DNA polymerase, are added. After homogenization, 100 μL are deposited on microfluidic cards containing the probes corresponding to the genes tested; these are centrifuged and then sealed. The CD ROM corresponding to the profile of the genes deposited on the plates is loaded into SDS 2.3 software, specifying the placement of each gene on the card. The control gene (or "endogenous gene") to use for normalization of results is indicated before the start of PCR. This is done according to the protocol provided by Applied Biosystems in the ABI Prism 7900HT Sequence Detection System. The qPCR steps are 2 min at 50° C., 10 min at 94.5° C. then 30 s at 97° C. and 1 min at 59.7° C. for 40 cycles.

Statistical Analyses

Real-time quantitative PCR can be used if its efficacy is comprised between 90% and 110%. For each sample, the number of cycles at which the signal appears is determined by the SDS 2.3 software. For the same test, the expression levels of transcripts of interest obtained are normalized relative to the value obtained for the beta-2-microglobulin housekeeping gene. This gene, whose expression is constitutive and invariant, makes it possible to overcome any variations induced during the experiment (total RNA assay, pipetting, reverse transcription step, PCR in the device).

In the RT-PCR TLDA method, quantification is done using the ΔΔCt comparative method. The relative quantification (RQ) values obtained correspond to the amplitude level (x times more or less than the control) of expression relative to our control, not irradiated here. The RQ is obtained by the following calculation, where the control is equal to 1:

$$RQ=2^{-\Delta\Delta Ct}=2^{-(\Delta Ct\ treated-\Delta Ct\ untreated)}$$

ΔCt treated=Ct treated target gene–Ct treated housekeeping gene

ΔCt untreated=Ct untreated target gene–Ct untreated housekeeping gene

In order to assess statistically significant variations of transcription activity, we will use Student's t-test. Each condition is done in triplicate (3 untreated and 3 treated under the same conditions). Fisher's F test is first applied by comparing the two data matrices. When the value is greater than α=0.05 then the variance for the Student's t-test is 2, when the Fisher's F-test is less than α=0.05, then the variance will be equal to 3. The transcriptional variations used will be those that correspond to a Student's t-test of less than α=0.05.

The results are shown by mean over n=3. Student's t-test was used to compare the effect between treated and untreated cells.

The results are considered significant for p<0.05(*) or p<0.01(**).

The tables of results below show the effect of Probiophyte LB on several keratinocyte (NHK) genes complementary to those of the preceding study, and on several melanocyte (NHM) and fibroblast (NHF) genes.

Values less than 1 correspond to an inhibitor effect on the expression of said genes and values greater than 1 correspond to a stimulant effect on the expression of said genes.

TABLE 4

Results on gene expression of melanocytes

| Biological domains | Gene | Symbol | NCBI Reference | Gene expression of melanocytes | |
|---|---|---|---|---|---|
| | | | | Probiophyte LB 0.1 μg/mL | Probiophyte LB 0.2 μg/mL |
| Melanogenesis | Peroxisome proliferator activated receptor gamma | PPARG | Gene ID: 5468 | — | 0.809 |

TABLE 5

Results on gene expression of keratinocytes

| Biological domains | Genes | Symbols | NCBI Reference | Gene expression of keratinocytes | |
|---|---|---|---|---|---|
| | | | | Probiophyte LB 0.1 µg/mL | Probiophyte LB 0.2 µg/mL |
| Extracellular matrix | Metallopeptidase 9 | MMP9 | Gene ID: 4318 | 0.692 | 0.668 |
| Innate immunity | Toll-like receptor 1 | TLR1 | Gene ID: 7096 | — | 2.587 |

TABLE 6

Results on gene expression of fibroblasts

| Biological domains | Genes | Symbols | NCBI Reference | Gene expression of fibroblasts | |
|---|---|---|---|---|---|
| | | | | Probiophyte LB 0.1 µg/mL | Probiophyte LB 0.2 µg/mL |
| Extracellular matrix and cell-matrix interactions | Collagen 1A1 | COL1A1 | Gene ID: 1277 | 1.759 | — |
| | Collagen 5A1 | COL5A1 | Gene ID: 1289 | 1.288 | — |
| | Collagen 13A2 | COL13A1 | Gene ID: 1305 | 1.334 | — |
| | Elastin | ELN | Gene ID: 2006 | 1.203 | — |
| | Cysteine-Rich, Angiogenic Inducer, 61 (IGF-Binding Protein 10) | CYR61 | Gene ID: 3491 | 1.237 | — |
| | Integrin beta 1 | ITGB1 | Gene ID: 3688 | 1.216 | — |
| Hydration | Aquaporin 1 | AQP1 | Gene ID: 358 | 1.270 | — |
| | Hyaluronan synthase 2 | HAS2 | Gene ID: 3037 | 1.188 | — |
| | Hyaluronan synthase 3 | HAS3 | Gene ID: 3038 | 1.799 | — |
| | Hyaluronate receptor | CD44 | Gene ID: 960 | 1.246 | — |
| | ATP Binding Cassette Subfamily C Member 5 | ABCC5 | Gene ID: 10057 | 1.376 | — |
| Proliferation and differentiation | Proliferation marker Ki-67 | MKi67 | Gene ID: 4288 | 1.680 | — |
| | Latent transforming growth factor beta binding protein 1 | LTBP1 | Gene ID: 4052 | 1.429 | — |
| Antioxidant protection and detoxification | Glutathione peroxidase 1 | GPX1 | Gene ID: 2876 | — | 1.231 |
| | Multidrug-Resistance like Protein 1 | ABCC1 | Gene ID: 4369 | 1.313 | — |
| | Mitochondrial ATP-dependent serine peptidases | LONP1 | Gene ID: 9361 | — | 1.159 |
| Hypoxia and energy | Hypoxia inducible factor 1 alpha | HIF1a | Gene ID: 3091 | 1.183 | — |
| | Solute carrier family 2 (facilitated glucose transporter), member 1 | SLC2A1 | Gene ID: 901 | 1.097 | — |
| | Mitochondrially encoded ATP synthase 6 | MT | Gene ID: 101928524 | — | 1.359 |
| Cell structures | Lamin A | LMNA | Gene ID: 4000 | 1.242 | — |
| | Nesprin-2 | SYNE2 | Gene ID: 23224 | 1.524 | — |
| | Myosin X | MYO10 | Gene ID: 4651 | 1.275 | — |

These results show that dermal fibroblasts are much more sensitive to modulation of their genes by Probiophyte LB (n=22 genes modulated) than keratinocytes (n=2 genes modulated) and melanocytes (n=1 gene modulated). The extract therefore has a very substantial activity in dermal cells.

For dermal fibroblasts, in particular, activation is observed by the *Lactobacillus rhamnosus* lysate of the invention of the genes involved in:

cell-matrix adhesion and cohesion that allows the fibroblast to densify and contract the matrix with the positive effects of this process on firmness (ITGB1);

maintenance of the integrity of cell structures such as the nucleus, and therefore on the resistance of skin cells (SYNE2, LMNA);

formation of several collagens and elastin which are major constituents of the dermis and whose stimulation opposes the effects of aging (COL1A1, COL5A1, COL13A1, ELN);

the water balance of the dermis relative to water movement (AQP1) or water reserves, with formation (HAS2 and 3), fixation (CD44) and secretion (ABCC5) of hyaluronic acid, which can hold up to 1000 times its weight in water;

dermal cell regeneration (Ki67)

cell antioxidant defenses (GPX1) and detoxifiers (ABCC1=MRP1). This gene codes for a protein that will make it possible to expel compounds from the cell that can be toxic to it;

adaptation of cells to conditions of hypoxia (HIF1a) which increase with skin age (see hypoxia markers such as carbonic anhydrase 9 in aged skin) and which can be explained by the reduction of the dermal vascular network with age;

energy and nutrition with the entry of glucose into cells (SLC2A1);

production of energy in the mitochondria (MT=NADH dehydrogenase or ubiquinone);

detoxification and therefore protection of the mitochondria by degradation and recycling of damaged mitochondrial proteins (LONP1).

The following is observed for keratinocytes:

activation of a gene involved in innate immunity (TLR1) and which is an immune surveillance receptor for bacterial constituents such as lipopeptides inhibition of a gene involved in collagen degradation (MMP9), processes that increase with aging.

The following is observed for melanocytes:

reduction of a melanogenesis stimulating factor in these cells (PPARG) which contributes to a depigmenting effect.

All of the results show that the *Lactobacillus rhamnosus* extract (CNCM I-5313) according to the invention applied on keratinous materials, in particular the skin, make it possible to prevent and/or reduce loss of firmness and density of the skin, prevent and/or reduce the appearance of wrinkles and/or fine lines and/or skin spots, improve skin radiance and/or evenness, promote and/or improve skin hydration, detoxify the skin, stimulate its antioxidant defenses and/or improve resistance of the skin to hypoxia, and/or control skin microflora, and/or stimulate skin immunity and the formation of the skin barrier.

Example 3: Formulations

The following formulations are prepared according to the conventional formulation methods in the cosmetic field.

| Antiaging regenerating serum | |
|---|---|
| Water | qs 100% |
| Alcohol | 5% |
| Glycols | 8% |
| Isotridecyle isononanoate | 4% |
| Squalane | 2% |
| Caprylic/capric acid triglyceride | 2% |

| Antiaging regenerating serum | |
|---|---|
| Methyl gluceth-20: | 2% |
| Steareth-2: | 0.5% |
| Steareth-21: | 0.5% |
| Carbomer | 0.3% |
| Sodium hyaluronate | 0.2% |
| Xanthan gum | 0.1% |
| Sodium hydroxide | 0.1% |
| Adenosine | 0.04% |
| *L. rhamnosus* lysate | 2% |

Applied on the skin, the composition improves skin firmness and reduce wrinkles.

| Purifying mask | |
|---|---|
| Water | qs 100% |
| Kaolin | 18% |
| Stearic acid | 3.5% |
| Palmitic acid | 3.5% |
| Glycols | 6% |
| Titanium dioxide | 3% |
| Lauric acid | 2% |
| Glyceryl stearate | 1.5% |
| PEG-100 stearate | 1.5% |
| Potassium hydroxide | 1.4% |
| Phenoxyethanol | 0.7% |
| Acrylic polymer | 0.5% |
| Xanthan gum | 0.05% |
| *L. rhamnosus* lysate | 1% |
| Zinc gluconate | 0.05% |

Applied on the skin, the composition reduces sebum level, reduces pore size and improves skin texture.

| Antipollution detoxifying lotion | |
|---|---|
| Water | qs 100% |
| Glycols | 15% |
| Alcohol | 5% |
| Phenoxyethanol | 0.8% |
| PEG-60 hydrogenated ricin oil | 0.5% |
| Sodium hyaluronate | 0.1% |
| *L. rhamnosus* lysate | 0.5% |
| Prebiotic extract | 0.5% |

Applied on the skin, the composition confers a healthy glow and a radiant, even complexion to the skin.

| Lightening essence | |
|---|---|
| Water | qs 100% |
| Glycols | 11% |
| Propanediol | 5% |
| Dimethicone | 2% |
| Alcohol | 1% |
| Tromethamine | 1.5% |
| Phenoxyethanol | 0.9% |
| Acrylic copolymer | 0.6% |
| Sodium citrate | 0.5% |
| *L. rhamnosus* lysate | 2% |
| Ascorbyl glucoside (vitamin CG) | 0.5% |

Applied onto the skin, the composition improves evenness of the complexion.

| Radiance foundation | |
| --- | --- |
| Water | qs 100% |
| Hydrocarbon oils | 12% |
| Titanium dioxide | 10% |
| Propanediol | 5% |
| Glycerine | 5% |
| Zinc oxide | 3% |
| Surfactants | 3% |
| Film-forming polymer | 1% |
| Potassium sorbate | 0.1% |
| L. rhamnosus lysate | 1% |

Applied on the skin, the composition confers a healthy glow and a radiant, even complexion.

| Vitamin serum | |
| --- | --- |
| Glycerol | 4% |
| Butylene glycol | 3% |
| Carbomer | 0.5% |
| Lactic acid | 1% |
| L. rhamnosus lysate | 2% |
| Sodium hydroxide | 0.7% |
| Xanthan gum | 0.1% |
| Acrylic gelling agent | 0.2% |
| Alcohol | 3% |
| Ascorbyl glucoside (vitamin CG) | 0.5% |
| Phenoxyethanol | 0.5% |
| Dyes | qs % |
| Water | qs 100% |

Applied on the skin, the composition improves skin firmness and confers a healthy glow.

| Mist | |
| --- | --- |
| Glycerol | 2% |
| Glycols | 4% |
| Gelling agents | 2% |
| L. rhamnosus lysate | 1% |
| Caprylic/capric acid triglycerides | 0.25% |
| Emulsifiers | 0.6% |
| Phenoxyethanol | 0.5% |
| Tocopherol (vitamin E) | 0.02% |
| Water | qs 100% |

Applied on the skin, the composition promotes and/or improves the nutrition of the skin and confers a healthy glow and a radiant and even complexion.

The invention claimed is:

1. A non-therapeutic cosmetic method intended to prevent and/or reduce the signs of skin aging and/or promote and/or improve the barrier function, comprising the application on keratinous materials of at least one *Lactobacillus rhamnosus* CNCM I-5313 lysate or one of its fractions, or a composition comprising, in a physiologically-acceptable medium, at least one *Lactobacillus rhamnosus* CNCM I-5313 lysate or one of its fractions and at least one excipient chosen from among solvents other than water, surfactants, gelling agents, thickeners, fillers, dyes, film-forming polymers, fragrances, and mixtures thereof.

2. A non-therapeutic cosmetic method according to claim 1, for preventing and/or reducing loss of skin firmness and/or density, reducing the appearance of wrinkles and/or fine lines and/or skin spots, improving skin radiance and/or evenness, promoting and/or improving skin hydration, detoxifying the skin and/or improving resistance of the skin to hypoxia, and/or control skin microflora.

3. The non-therapeutic cosmetic method according to claim 1, wherein the composition is applied onto aged, lackluster, tired skin, or skin impacted by an unfavorable or unbalanced diet, emotional stress, or lack of sleep.

4. The non-therapeutic cosmetic method according to claim 1, wherein the fraction of the lysate is chosen from the group consisting of: the cell cytoplasm fraction, the cell wall constituents, and the cell membrane constituents.

5. The non-therapeutic cosmetic method according to claim 1, wherein the *Lactobacillus rhamnosus* CNCM I-5313 lysate is obtained by osmotic shock, thermal shock, ultrasound, and/or mechanical stress.

6. The non-therapeutic cosmetic method according to claim 1, wherein the lysate has a concentration of around 0.1 to 10% by weight of active dry matter relative to its total weight.

* * * * *